United States Patent
Keren et al.

(10) Patent No.: US 7,766,892 B2
(45) Date of Patent: Aug. 3, 2010

(54) APPARATUS AND METHODS FOR TREATING CONGESTIVE HEART DISEASE

(76) Inventors: Gad Keren, 11 Simcha Holzberg Street, 55000 Kiryat Ono (IL); Ascher Shmulewitz, 88 Guy Pl., Apt. 301, San Francisco, CA (US) 94107; Benjamin Spenser, Hagefen 5 Street, 30900 Zichron Ya'acov (IL); Michael Arad, 32 Remez Street, 62192 Tel Aviv (IL); Randy J. Kesten, 181 Ada Ave., #41, Mountain View, CA (US) 94043; Sophia Pesotchinsky, 12755 Alto Verde La., Los Altos, CA (US) 94022; Michael H. Rosenthal, 783 Tolman Dr., Palo Alto, CA (US) 94305; Andrew W. Kramer, 698 N. Santa Cruz Ave., Los Gatos, CA (US) 95030; Sam G. Payne, 2175 Hoover Dr., Santa Clara, CA (US) 95051

( * ) Notice: Subject to any disclaimer, the term of this patent is extended or adjusted under 35 U.S.C. 154(b) by 1546 days.

(21) Appl. No.: 10/153,050

(22) Filed: May 21, 2002

(65) Prior Publication Data

US 2002/0169413 A1 Nov. 14, 2002

Related U.S. Application Data

(60) Division of application No. 09/562,493, filed on May 1, 2000, which is a continuation-in-part of application No. 09/229,390, filed on Jan. 11, 1999, now Pat. No. 6,749,598.

(51) Int. Cl.
*A61M 31/00* (2006.01)

(52) U.S. Cl. ...................................... 604/509
(58) Field of Classification Search ............ 604/101.05, 604/101.01, 99.01, 99.02, 99.03, 96.01, 912, 604/919, 914, 920, 103.04, 500, 508, 509; 606/194
See application file for complete search history.

(56) References Cited

U.S. PATENT DOCUMENTS

| | | | | |
|---|---|---|---|---|
| 4,546,759 A | * | 10/1985 | Solar | 600/18 |
| 4,636,195 A | * | 1/1987 | Wolinsky | 604/509 |
| 4,753,238 A | * | 6/1988 | Gaiser | 606/195 |
| 5,505,701 A | * | 4/1996 | Anaya Fernandez de Lomana | 604/101.03 |
| 5,599,307 A | * | 2/1997 | Bacher et al. | 604/101.05 |
| 5,779,673 A | * | 7/1998 | Roth et al. | 604/101.03 |
| 5,833,650 A | * | 11/1998 | Imran | 604/509 |
| 6,086,527 A | * | 7/2000 | Talpade | 600/18 |
| 2002/0099332 A1 | * | 7/2002 | Slepian et al. | 604/96.01 |

* cited by examiner

*Primary Examiner*—Matthew F Desanto
(74) *Attorney, Agent, or Firm*—Yvonne M. Horton

(57) ABSTRACT

Methods and apparatus are provided for treating congestive heart by actively or passively enhancing perfusion to the renal arteries. A first embodiment comprises a specially configured balloon catheter and extracorporeal pump, wherein the pump operates in a "once-through" fashion or alternating volume displacement mode. In another embodiment the catheter includes a pair of balloons to isolate a region of the aorta, and a third balloon that directs flow into the renal arteries. In still further embodiments, a stent or cuff having a constricted region is deployed in or around the aorta, respectively, to create a backpressure upstream of the stent or cuff. Methods of enhancing renal perfusion also are provided.

2 Claims, 17 Drawing Sheets

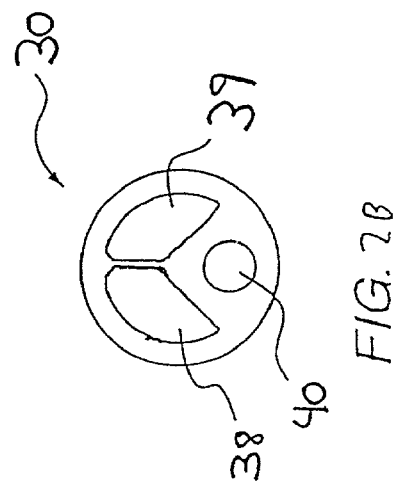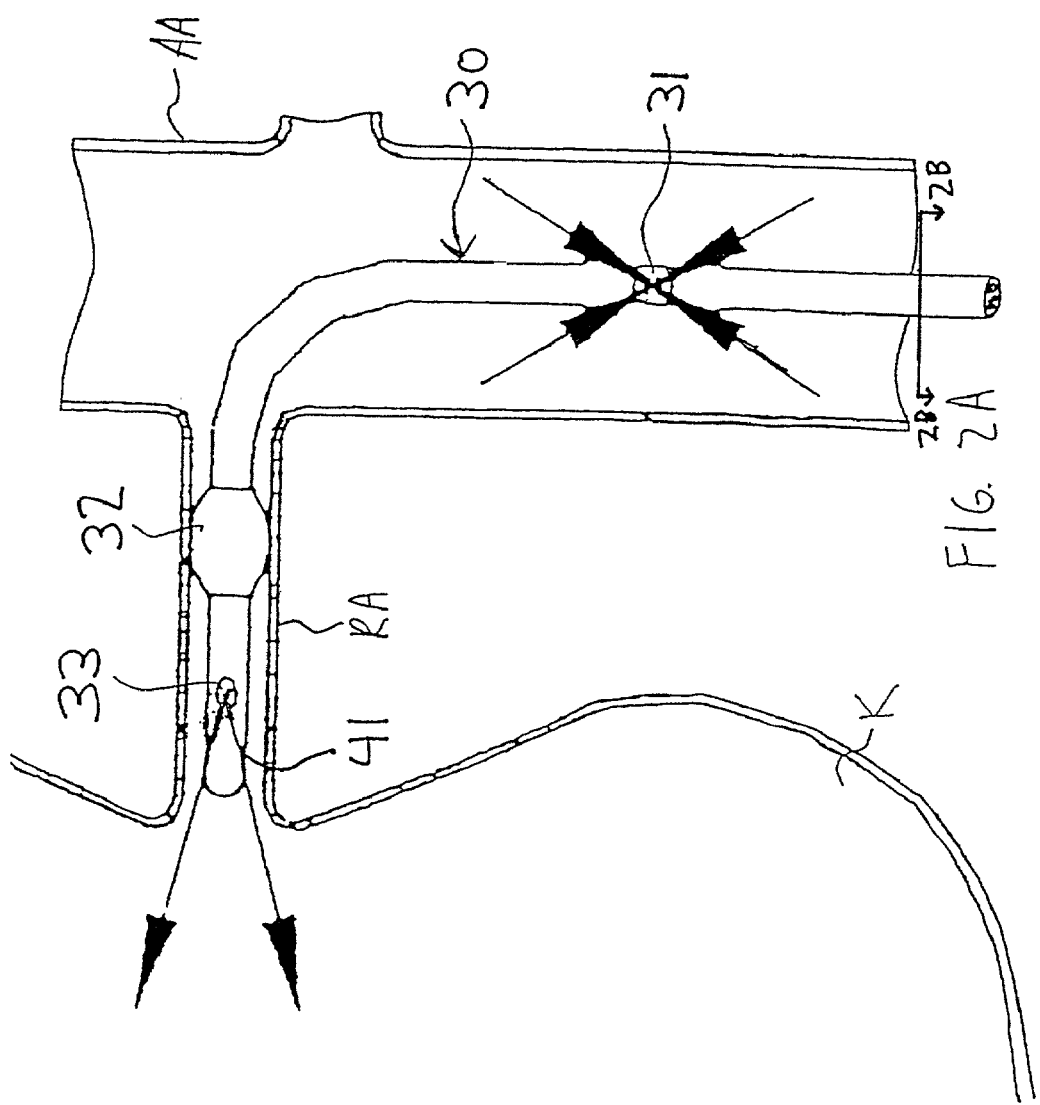

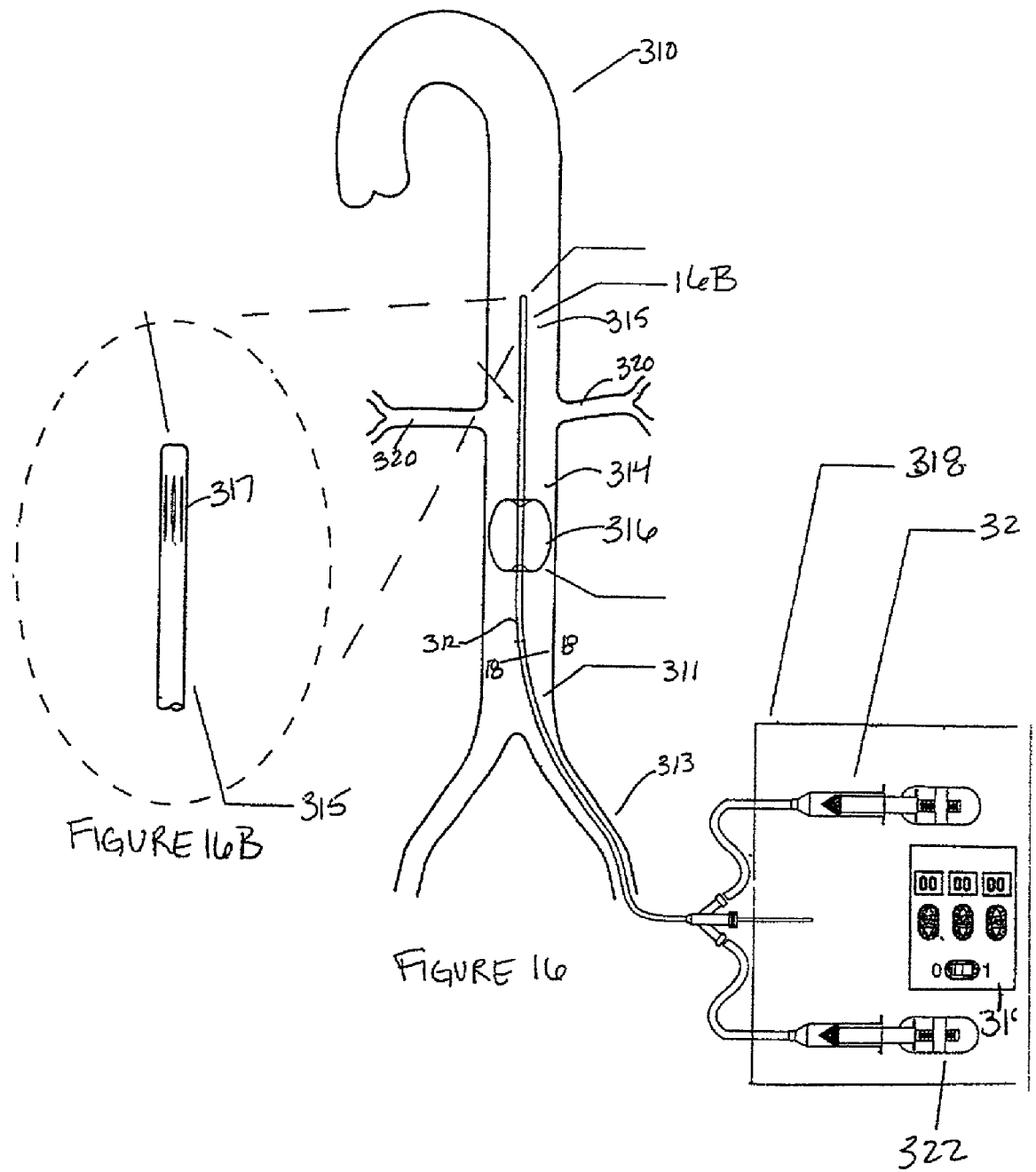

APPARATUS AND METHODS FOR TREATING CONGESTIVE HEART DISEASE

REFERENCE TO RELATED APPLICATION

This application is a divisional of application Ser. No. 09/562,493, filed May 1, 2000, which is a continuation-in-part of application Ser. No. 09/229,390, filed Jan. 11, 1999 now U.S. Pat. No. 6,749,598, incorporated herein by reference.

FIELD OF THE INVENTION

The present invention relates to apparatus for treating acute renal failure such as that caused by congestive heart disease and other trauma by providing increased blood perfusion to the kidneys, thereby enhancing renal function.

BACKGROUND OF THE INVENTION

Acute renal failure ("ARF") is an abrupt decrease in the kidney's ability to excrete waste from a patient's blood. This change in kidney function may-be attributable to many causes. A traumatic event, such as hemorrhage, gastrointestinal fluid loss, or renal fluid loss without proper fluid replacement may cause the patient to go into ARF. Patient's may also become vulnerable to ARF after receiving anesthesia, surgery, α-adrenergic argonists or high dose dopamine or patients with hepatorenal syndrome because of related systemic or renal vasoconstriction. Alternatively, systemic vasodilation cause by anaphylaxis; antihypertensive drugs, sepsis or drug overdose may also cause ARF because the body's natural defense is to shut down "non-essential" organs such as the kidneys. Additionally, reduced cardiac output caused by cardiac shock, congestive heart failure, pericardial tamponade or massive pulmonary embolism creates an excess of fluid in the body. Specifically it has long been known that cardiac dysfunction induces a series of events that ultimately contribute to congestive heart failure ("CHF"). One such event is a reduction in renal blood flow due to reduced cardiac output. This reduced flow can in turn result in the retention of excess fluid in the patient's body, leading for example, to pulmonary and cardiac edema.

The appearance of ARF significantly increases mortality. ICU patients mortality rates for patients without ARF are approximately 20%. However, once ARF is achieved, the mortality rates jump to between 60% and 80%. Preventing ARF in patients at risk but who have not yet had any renal insufficiency will have a dramatic impact on ICU mortality rates.

Chapter 62 of *Heart Disease: A Textbook of Cardiovascular Medicine*, (E. Braunwald, ed., 5th ed. 1996), published by Saunders of Philadelphia, Pa., reports that for patients with CHF, the fall in effective renal blood flow is proportional to the reduction in cardiac output. Renal blood flow in normal patients in an age range of 20-80 years averages 600 to 660 ml/min/m² corresponding to about 14 to 20 percent of simultaneously measured cardiac output. Within a wide spectrum of CHF severity, renal blood flow is depressed to an average range of 250 to 450 ml/min/m².

Previously known methods of treating AFF attributable to congestive heart failure and deteriorating renal function in patients having CHF principally involve administering drugs, including diuretics that enhance renal function, such as furosemide and thiazide; vasopressors intended to enhance renal blood flow, such as Dopamine; and vasodilators that reduce vasoconstriction of the renal vessels. Many of these drugs, when administered in systemic doses, have undesirable side-effects. Additionally, many of these drugs would not be helpful in treating other causes of ARF. Specifically, administering vasodilators to dilate the renal artery to a patient suffering from systemic vasodilation would merely compound the vasodilation system wide.

In addition, for patients with severe CHF (e.g., those awaiting heart transplant), mechanical methods, such as hemodialysis or left ventricular assist devices, may be implemented. Mechanical treatments, such as hemodialysis, however, generally have not been used for long-term management of CHF. Such mechanical treatments would also not be help for patients with strong hearts suffering from ARF.

Advanced heart failure ("HF") requires the combination of potent diuretics and severe restriction of salt intake. Poor patient compliance is a major cause of refractoriness to treatment. On the other hand, as renal urine output decreases with reduced renal perfusion, in the event of dehydration, the required diuretic dosages increase.

Recent work has focused on the use of intra-aortic balloon pumps (IABPs) to divert blood flow into the renal arteries. One such technique involves placing an IABP in the abdominal aorta so that the balloon is situated slightly below (proximal to) the renal arteries. The balloon is selectively inflated and deflated in a counterpulsation mode so that increased pressure distal to the balloon directs a greater portion of blood flow into the renal arteries.

In view of the foregoing, it would be desirable to provide methods and apparatus for treating and managing ARF without administering high doses of drugs or dehydrating the patient.

It further would be desirable to provide methods and apparatus for treating and managing ARF by improving blood flow to the kidneys, thereby enhancing renal function. Specifically, a system which could be used for all ARF patients during critical treatment times would be beneficial. In particular, a system which could be placed easily in a patient during emergency or critical care without the need for surgery or X-ray fluoroscopy guidance would be useful to all patients in danger of ARF.

It also would be desirable to provide methods and apparatus for treating and managing ARF that permit the administration of low doses of drugs, in a localized manner, to improve renal function without having an effect system wide.

It still further would be desirable to provide methods and apparatus for treating and managing ARF using apparatus that may be percutaneously and transluminally implanted in the patient.

SUMMARY OF THE INVENTION

The present invention provides methods and apparatus for treating and managing ARF without administering high doses of drugs or dehydrating the patient by improving blood flow to the kidneys, thereby enhancing renal function.

This invention also provides methods and apparatus for treating and managing ARF that permit the administration of low doses of drugs, in a localized manner, to improve renal function.

The present invention also provides methods and apparatus for treating and managing ARF using apparatus that may be percutaneously and transluminally implanted in the patient.

These and other advantages of the present invention are obtained by providing apparatus and methods that either actively or passively enhance perfusion of the renal arteries with autologous blood. Active perfusion may be accomplished using an extracorporeal pump and one of a number of specially designed catheter sets, while passive perfusion may be accomplished by creating a constriction in the aorta proximal to the renal arteries. Apparatus and method which direct a low dose of drugs in a localized manner are also provided.

To facilitate the advancement of the catheter into the patient's coronary artery, a guiding catheter having a distal tip may be first percutaneously introduced into the abdominal aorta of a patient by the Seldinger technique through the brachial or femoral arteries. The catheter is advanced until the preshaped distal tip of the guiding catheter is disposed within the aorta adjacent the ostium of the renal arteries. A balloon catheter embodying features of the invention may then be advanced through the guiding catheter into the patient's abdominal aorta over a guidewire until the balloon on the catheter is disposed at the desired region of the patient's artery. In specific embodiments, the use of a guiding catheter is unnecessary. The advancement of the catheter over a guidewire is sufficient to achieve adequate placement.

For active perfusion, the apparatus of the present invention preferably comprises a balloon catheter coupled to a pump. The pump may be extracorporeal or in-line. In one embodiment the catheter has an inlet end configured for placement in a source of arterial blood, such as the aorta or a femoral artery, and an outlet end configured to provide perfusion of one or both renal arteries. Blood is drawn through the catheter from the inlet end and pumped back, using either the same or a different lumen, to one or both renal arteries. Blood drawn into the catheter either may pass through the extracorporeal pump, or alternatively the pump may operate by periodic fluid displacement. Sensors may be provided on the catheter to monitor pressure within the renal arteries, and such pressure data may in turn be used to adjust the pump operation. The balloon catheter has at least one balloon. In specific embodiments, the balloon catheter has 2 balloons. The balloons may be systematically inflated against the aorta wall and deflated to assist in the perfusion of the renal arteries.

The balloon may be formed using either compliant or non-compliant materials, preferably compliant. Most optimally, the balloon material is chosen so that inflation of the balloon to a volume sufficient to occlude the aorta, i.e., to a diameter of between 15 and 35 mm, will create a sufficient pressure within the balloon so as to provide the balloon with some degree of mechanical rigidity and to likewise apply a small amount of outward radial force to the aortic wall so as to provide positional and orientational stability to the balloon. Such a pressure is typically between about 4 and about 20 psi. Materials that can achieve such behavior include synthetic polyisoprene and thermoplastic urethane. Material durometer and tensile modulus must be selected appropriately so as to allow for the above properties to be exhibited with a practical balloon-wall thickness. Material with a shore hardness of about 70 A to about 100 A, preferably about 80 A to about 90 A are appropriate. For example, thermoplastic urethane such as Dow Pellethane 2363-80 A, which has a Shore hardness of 80 A, a tensile modulus of 1750 psi at 300% elongation and an ultimate elongation of 550%, can be used for forming the balloon. Balloons may be formed by dipping a shaped mandrel into a mixture of urethane dissolved in a solvent, such as tetrahydrofuran. The mandrel should be shaped so as to produce an uninflated balloon with a diameter of between 3 and 8 mm. The dipping process should be repeated so as to produce a balloon with an uninflated wall thickness of between 0.002 in. and 0.010 in. Alternatively, the balloon can be formed by first melt-extruding a length of tubing and then blow-molding the tube into a balloon form. Dimensions of the tubing and mold would be chosen to achieve the same diameter and thickness described above.

The inflated balloon should have a maximum safety-factored diameter of between 15 and 35 mm, to accommodate the range of diameters of the human infrarenal aorta. Alternatively, the device could be available in a range of balloon sizes, such as 15 to 25 mm and 25 to 35 mm. In order to provide positional and orientational stability to the catheter within the aorta, the inflated balloon should have a length of about 2 to about 8 cm, preferably about 3 to about 6 cm. The catheter shaft can be formed by melt extrusion processing of thermoplastic polymers typically used in catheters, such as Hytrel, Pebax or polyurethane.

The balloon can be attached to the catheter shaft by either an adhesive bond or a thermal fusion. The later can be used if a thermoplastic balloon material, such as polyurethane, is used. If a thermoset material, such as polyisoprene, is used, an adhesive will be used to attach the balloon. Cyanoacrylate adhesives, such as Loctite 4203 combined with Loctite Primer 770, can be used, as can urethane-based UV-cured adhesives, such as Dymax 205CTH can also be used. In addition, 2-part adhesives, such as epoxies or urethane-based adhesives can be used.

In a specific embodiment, the catheter has a pump which is an in-line archimedean screw pump situated within a balloon catheter. An archimedean screw is a screw which allows for fluid movement with the turning of the screw. The balloon catheter has 2 balloons, a distal balloon and a proximal balloon, longitudinally displaced from each other, and the screw pump is preferably situated between the two balloons. However, the screw pump may also be situated at a location distal to the distal balloon. The catheter is placed in the patient within the abdominal aorta. The balloon catheter has a proximal end and a distal end. The catheter distal end is inserted below the renal arteries, specifically the femoral artery, in the patient and advanced until the distal balloon is situated above the renal arteries. Below the renal arteries is defined as toward the patients legs, and above is defined as toward the patient's head. However, in certain embodiments, it may be preferable to enter the patient from above the renal arteries, for example from the brachial arteries. If so, then the placement of the balloons and any blood or drug outlet ports would be inverted on the catheter shaft with respect to any description of preferred embodiments in this application. A blood inlet is located on a portion of the catheter distal end that is distal to the distal balloon. In the specific embodiment, the screw pump is activated, causing blood to enter the catheter through the blood lumen. The screw pump causes a pressure increase in the blood, which then exits the catheter through outlet ports near the renal arteries. Alternatively, some blood may exit the catheter at the proximal end to provide blood to the lower extremities. The balloons may be inflated and deflated to provide blood flow to the patient's lower extremities.

The balloon of the catheter is inflated to retain the outlet end of the catheter in position in a renal artery and to prevent backflow of blood into the abdominal aorta. Alternatively, a pair of balloons may be selectively inflated to isolate the region of the abdominal aorta adjacent to the renal arteries. In yet another embodiment, a center balloon is disposed within an isolated region of the abdominal aorta defined by the distal and proximal balloons, and the extracorporeal pump is employed to inflate the third balloon to increase flow to the renal arteries.

In any of the foregoing cases it is expected that blood passing through the catheter, or trapped within the isolated region of the abdominal aorta, will have a higher pressure and flow rate than blood reaching the renal arteries via the abdominal aorta. This, in turn, is expected to improve renal blood flow without the administration of systemic drug doses.

The enhanced renal blood flow is expected to provide a proportional increase in renal function, thereby reducing fluid retention.

In further alternative embodiments, the catheter may include a drug infusion reservoir that injects a low dose of a drug (e.g., a diuretic or vasodilator) into blood flowing through the lumen, so that the drug-infused blood passes directly into the kidneys, or separate catheters to perfuse the left and right kidneys independently.

In a specific embodiment, a balloon catheter having a distal end and a proximal end and at least one lumen therebetween is inserted in a patient below the renal arteries, specifically the femoral artery. The catheter includes a balloon disposed about the catheter shaft. The catheter is advanced until the distal end sits above the renal arteries and the balloon sits at a location below the renal arteries within the patient's abdominal aorta. A drug delivery device is connected to the proximal end of the catheter. The drug delivery device may be extracorporeal or in-line. In specific embodiments, the catheter has at least two lumens. One lumen is an inflation lumen, in fluid communication with the interior of the balloon. The second lumen is an drug delivery lumen, which is in fluid communication with the drug delivery device and with discharge ports which are located on the catheter shaft at a location distal to the balloon. In some embodiments, a third lumen may exist, which is the blood lumen. The blood lumen would have an inlet port on the catheter shaft distal end and an outlet port at a location proximal to the balloon.

After placement, the balloon is inflated. When the balloon is inflated against the abdominal aorta wall, the drug delivery device is activated. A drug is delivered through the drug delivery lumen, and the drug enters the patients aorta through the discharge points. Because of the inflated balloon sitting just below the renal arteries, the drug is effectively blocked from entering the lower extremities, and instead flows to the renal arteries. In certain embodiments, the drug is delivered in a pulse fashion, with the balloon inflating at drug delivery and deflating to allow blood to flow between drug delivery pulses.

For passive perfusion, apparatus is provided that constricts the abdominal aorta proximal to the renal arteries. In this case, a stent or other device is disposed within the aorta to cause a narrowing of the aorta proximal to the renal arteries, thereby creating a pressure differential across the apparatus that is expected to improve blood flow rate to the renal arteries.

Methods of using the apparatus of the present invention for treating ARF are also provided.

BRIEF DESCRIPTION OF THE DRAWINGS

Further features of the invention, its nature and various advantages will be more apparent from the accompanying drawings and the following detailed description of the preferred embodiments, in which:

FIGS. 2A and 2B are, respectively, a side view of the distal end of the apparatus of the apparatus of FIG. 1, and a cross-sectional view of the apparatus along section line 2B-2B of FIG. 2A;

FIG. 6 is a partial sectional view of a human circulatory system having an alternative embodiment of the apparatus of FIG. 1 in which blood is pumped using periodic fluid displacement;

FIG. 16 is an elevational view of a catheter embodying features of the invention including a drug delivery system disposed with a patient's abdominal aorta, FIG. 16B is an enlarged view of area 16B.

DETAILED DESCRIPTION OF THE INVENTION

The present invention provides several apparatus for treating patients suffering from congestive heart failure ("CHF") by improving renal blood flow and renal function. Some preferred embodiments of the present invention provide active perfusion of the renal arteries, and comprise a catheter and an extracorporeal pump. The catheter and pump may be used either to withdraw autologous blood from the patient's body and reperfuse that blood into the patient's renal arteries, or to isolate a region of the, abdominal aorta and cause a pressure differential within the isolated region that causes perfusion of the renal arteries.

Other preferred embodiments of the present invention cause a constriction in the abdominal aorta downstream (proximal) of the renal arteries, so that the pressure differential resulting from the constriction preferentially perfuses the renal arteries.

Figure 1:
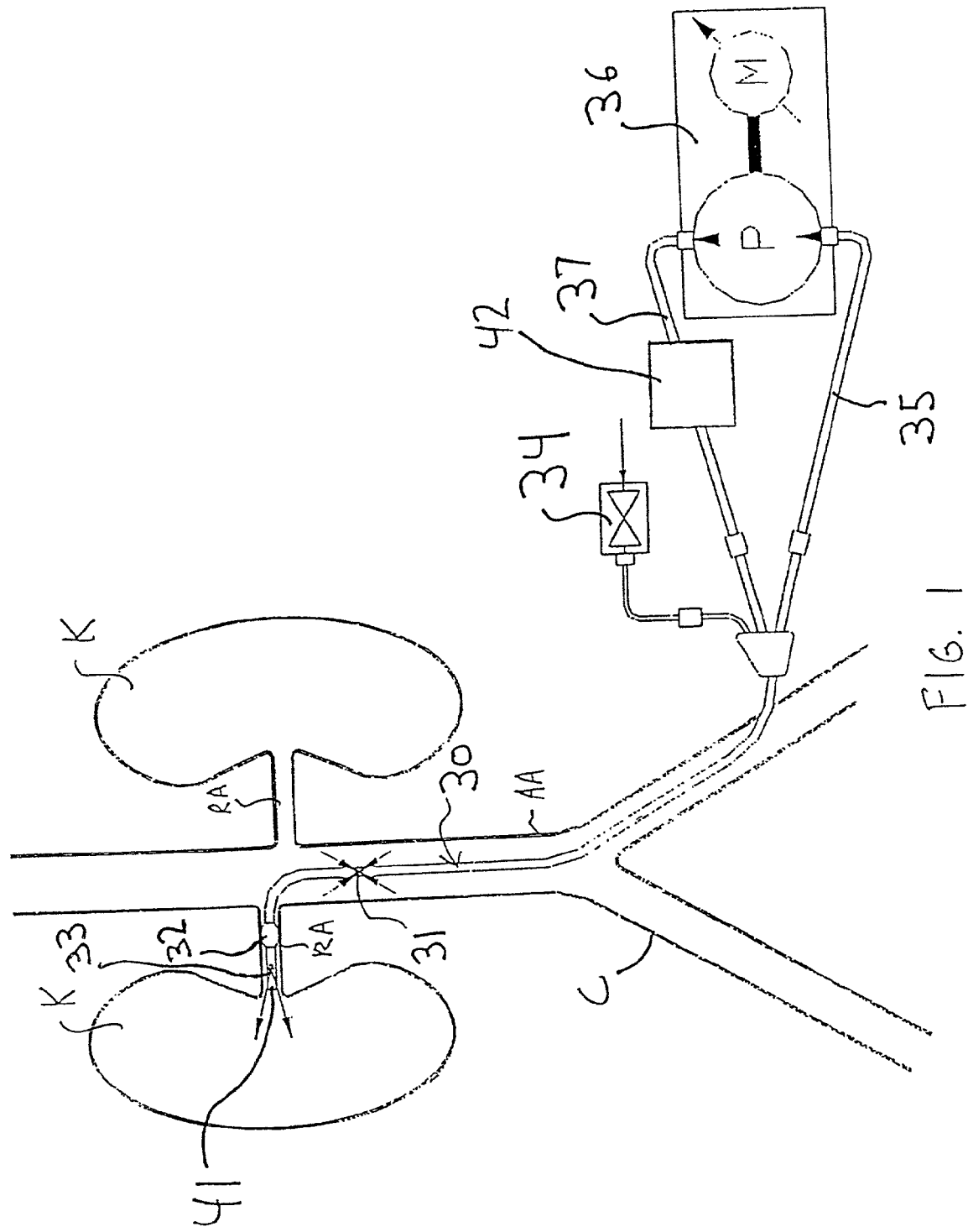
FIG. 1 is a partial sectional view of a human circulatory system having perfusion apparatus constructed in accordance with the principles of the present invention implanted therein.

Referring to FIGS. 1 and 2A-2B, a first illustrative embodiment of an active perfusion apparatus of the present invention comprising catheter and blood pump 36 is described.

Catheter 30 comprises a hollow flexible tube having inlet port 31, outlet port 33, and balloon 32. Ports 31 and 33 may optionally include one-way valves, such as duck-bill valves, that control the direction of flow. As shown in FIG. 2B, catheter 30 includes inlet lumen 38, outlet lumen 39 and inflation lumen 40. Catheter 30 preferably comprises a flexible biocompatible material typically used in catheter construction, such as polyethylene, polyurethane or nylon.

Balloon 32, which is configured to retain distal end 41 of catheter 30 in renal artery RA, is inflated and deflated using an inflation medium, e.g., saline, supplied by inflation device 34 through inflation lumen 40. Balloon 32 preferably comprises a compliant bio-compatible material, such as nylon. Inflation device 34 preferably comprises, e.g., a syringe, a pressurized cylinder or a pump.

Blood pump 36 is coupled in-line with catheter 30, and includes pump 36a driven by variable speed motor 36b. Blood pump 36 may comprise any of a number of previously known devices, such as a roller pump, centrifuge pump, or positive-displacement type pump. Blood pump 36 may in addition include control circuitry that receives signals from sensors disposed in catheter 30 to monitor local pressures, for example, renal and aortic pressure. Such monitored values may then be used by the control circuitry to adjust the perfusion pressure, blood flow rate or pump speed used to perfuse the kidneys.

Catheter 30 also optionally comprises a blood oxygenation element 42 disposed within the extracorporeal blood circuit. Oxygenation element 42, if provided, supplies oxygen to oxygen-poor blood prior to perfusion into renal artery RA. Oxygenation element 42 may comprise, for example, a blood oxygenator such as used in cardiopulmonary bypass. Alternatively, the blood perfused into the renal artery may be mixed with saline supersaturated with oxygen, for example, as described in U.S. Pat. No. 5,797,876, which is incorporated herein by reference.

In operation, blood enters catheter 30 through inlet port 31 and is drawn out of the patient's body through inlet lumen 39 to inlet tube 35 of pump 36. The blood then passes through blood pump 36, which controls the volume and pressure of blood delivered to the renal artery. Blood then passes through pump outlet tube 37, back through outlet lumen 39 of catheter 30, and is delivered to the renal artery through outlet port 33. As described hereinabove, operation of the blood pump may be adjusted responsive to pressure or flow parameters measured in the renal arteries, the aorta, or elsewhere within catheter 30.

Catheter 30 preferably is implanted in circulatory system C so that inlet port 31 is disposed in abdominal aorta AA, while outlet port 33 is disposed in renal artery RA. When balloon 32 inflates, it engages the walls of the renal artery and retains holes 31 and 33 in position. Balloon 32 also prevents backflow of high pressure blood exiting through outlet port 33 from flowing backwards into abdominal aorta AA. Accordingly, blood entering catheter 30 via inlet port 31 passes into the renal artery RA and kidney K through outlet port 33, thereby enhancing renal blood flow and renal function.

Figure 3:
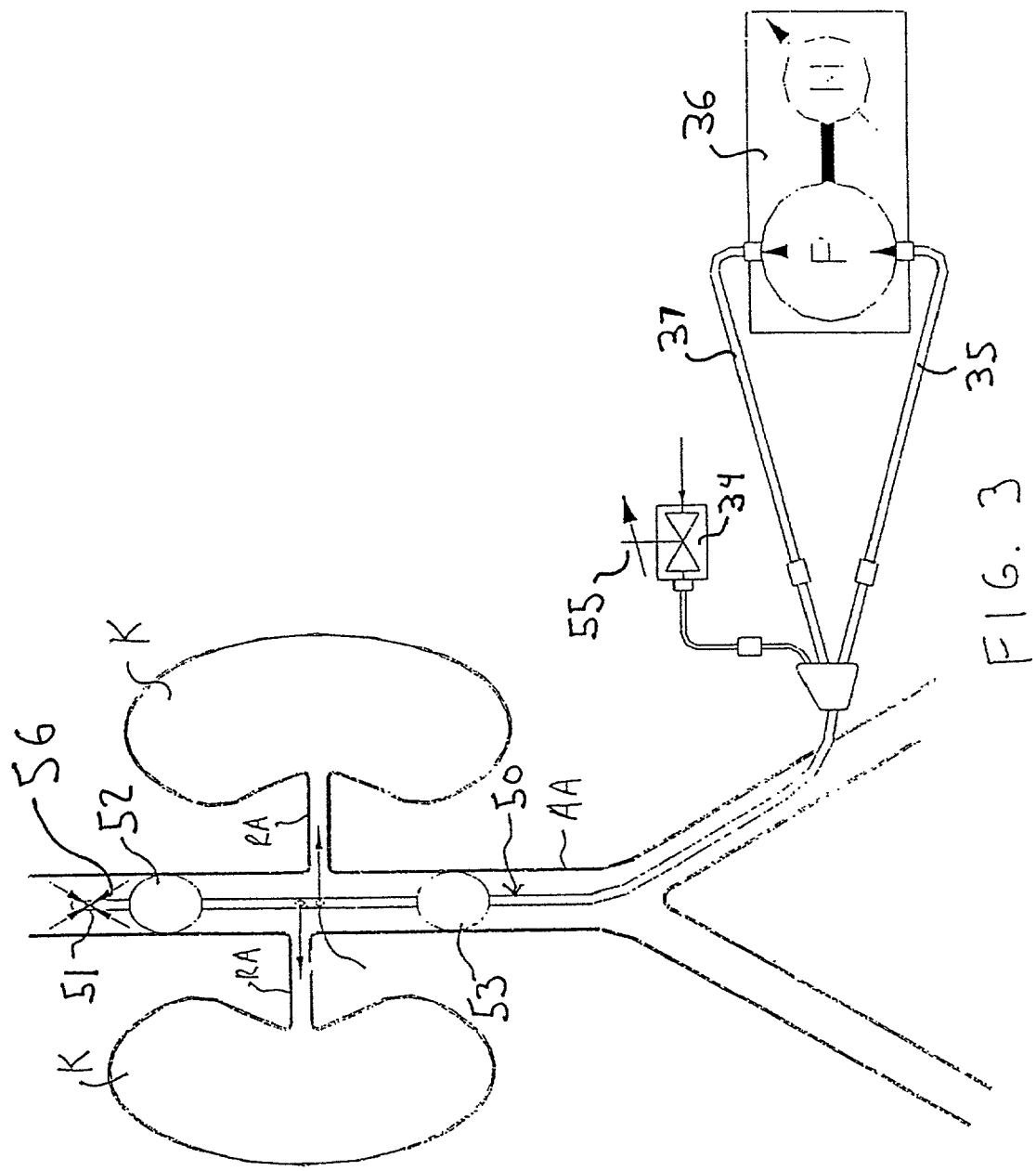
FIG. 3 is a partial sectional view of a human circulatory system having an alternative embodiment of the apparatus of FIG. 1 including a double balloon for simultaneous perfusion of both renal arteries.

Referring now to FIG. 3, an alternative embodiment of the active perfusion apparatus of the present invention, comprising catheter 50 and pump 36, is described. Catheter 50 is similar in construction to catheter 30 of FIGS. 1 & 2A-2B, and includes inlet lumen 38, outlet lumen 39, and inflation lumen 40. Catheter 50 is coupled to balloon inflation device 34, blood pump 36, including pump inlet tube 35 and pump outlet tube 37. Unlike catheter 30, however, distal region 56 of catheter 50 is disposed in the abdominal aorta, not the renal artery, and catheter 50 includes proximal balloon 53 in addition to balloon 52 located between inlet port 51 and outlet port 54.

In particular, inlet port 51 is disposed in distal region 56 of catheter 50, and again may optionally include a one-way flow valve. Outlet port 54 comprises several apertures communicating with outlet lumen 39, and may in addition optionally include one-way flow valves. The positions of the apertures forming outlet port 54 between balloons 52 and 53 and adjacent renal arteries RA ensures that the blood is deposited into both kidneys simultaneously, thereby enhancing renal blood flow and function.

Balloons 52 and 53 are inflated/deflated with an inflation medium, such as saline, using inflation device 34. When inflated, balloons 52 and 53 isolate the region of the aorta there between (including the renal arteries) from the remainder of the aorta. Consequently, blood exiting catheter 50 via outlet port 54 is directed into renal arteries RA. In addition, because for this embodiment inflation of the balloons 52 and 53 occludes blood flow to the patient's lower extremities, balloons 52 and 53 must be periodically deflated. Accordingly, inflation device 34 preferably comprises a pump that deflates balloons 52 and 53 at predetermined intervals, or is synchronized to the patient's heart rhythm via controller 55. In the latter case, controller 55 may comprise, for example, a previously known EKG device or blood oximeter.

In operation, catheter 50 is percutaneously and transluminally introduced in the patient's abdominal aorta via a cutdown to the femoral artery. Once catheter 50 is disposed so that balloons 52 and 53 straddle renal arteries RA, the balloons are inflated by inflation device 34. When inflated, the balloons hold inlet port 51 and outlet port 54 in position within aorta AA. The balloons also serve to prevent high pressure blood exiting through outlet port 54 from flowing out of the isolated region into other regions of the aorta. Blood pump 36 pumps blood through the fluid circuit from inlet port 51 to outlet port 54. Periodically, e.g., every 15 seconds, balloons 52 and 53 are deflated to re-establish blood flow to the lower extremities for a short period of time to prevent ischemia of the lower limbs.

Alternatively, balloons 52 and 53 may be connected to separate inflation lumens. In this embodiment, balloon 52 completely occludes aorta AA while balloon 53 is only partially inflated, thereby permitting some flow to the lower extremities during perfusion of the kidneys without periodic deflation of the balloons. Alternatively, balloon 53 may periodically be inflated/deflated to completely or partially occlude aorta AA independently of balloon 52.

Figure 4:
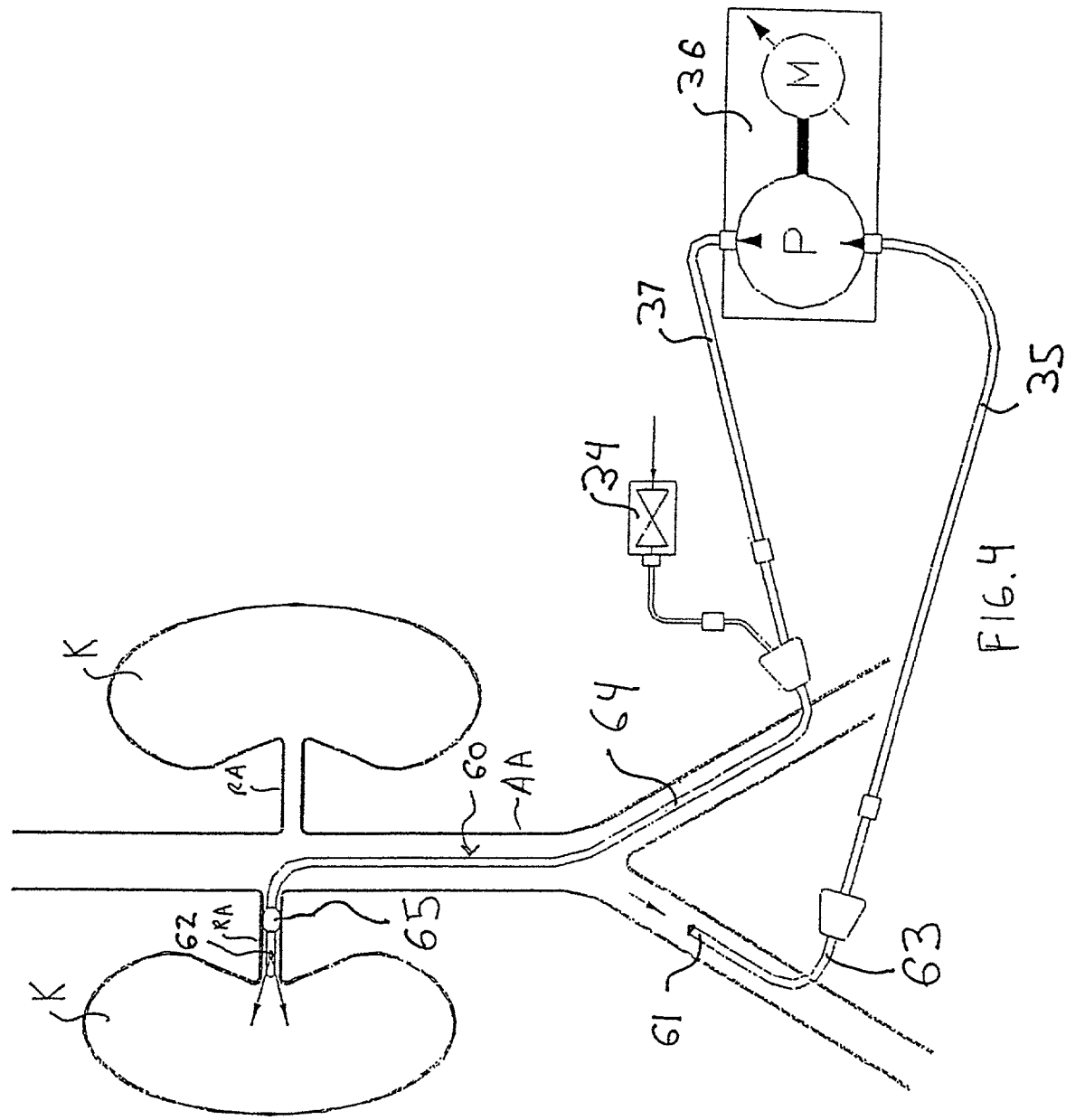
FIG. 4 is a partial sectional view of a human circulatory system having an alternative embodiment of the apparatus of FIG. 1 in which catheter blood flow occurs in one lumen.

Referring now to FIG. 4, a further alternative embodiment of an active perfusion apparatus is described that utilizes a single lumen for blood flow. Catheter 60 is similar in construction to catheter 30 of FIGS. 1 & 2A-2B and is coupled to inflation device 34 and blood pump 36, including pump inlet tube 35 and pump outlet tube 37. Because catheter 60 provides a "once-through" flow path, it includes only a single blood flow lumen and inflation lumen (thereby omitting, for example, outlet lumen 39 of FIG. 2B).

In particular, catheter 60 includes inlet line 63 having inlet port 61, and outlet line 64 having outlet port 62. Inlet line 63 is coupled to pump inlet pump 35, while outlet line 64 is coupled to pump outlet tube 37. Balloon 65 is disposed on outlet line 64, is configured to engage and retain outlet port 62 in renal artery RA, and is inflated with inflation medium injected via inflation device 34.

In operation, inlet line 63 is inserted into the patient's femoral artery, and outlet line then is inserted percutaneously and transluminally into aorta AA via a cut-down in the contralateral femoral artery. Balloon 65 is inflated to engage the walls of renal artery RA, retain outlet port 62 in position, and prevent backflow of high pressure blood into abdominal aorta AA. When blood pump 36 is activated, blood flows into inlet port 61, through inlet line 63 and pump inlet tube 35 to pump 36, and is returned by pump 36 through pump outlet tube 37, outlet line 64 and outlet port 62 into renal artery RA. Accordingly, blood entering catheter 60 via inlet port 61 passes into the renal artery RA and kidney K through outlet port 62, thereby enhancing renal blood flow and renal function.

Alternatively, inlet line 63 and outlet line 64 may be inserted in the same femoral artery. Also, the inlet and outlet lines may be incorporated into one concentric device. For example, a 9 Fr. pumping catheter may lie in the lumen of a 12 Fr. sheath; blood is pumped out of the body in the space between the catheter and the sheath and pumped back through the catheter. Additionally, blood may be removed from a vein instead of an artery. In this case, the venous blood may be oxygenated using an oxygenation element as described hereinabove with respect to FIG. 1. Temperature regulation also may be performed prior to blood perfusion into renal artery RA.

Figure 5:
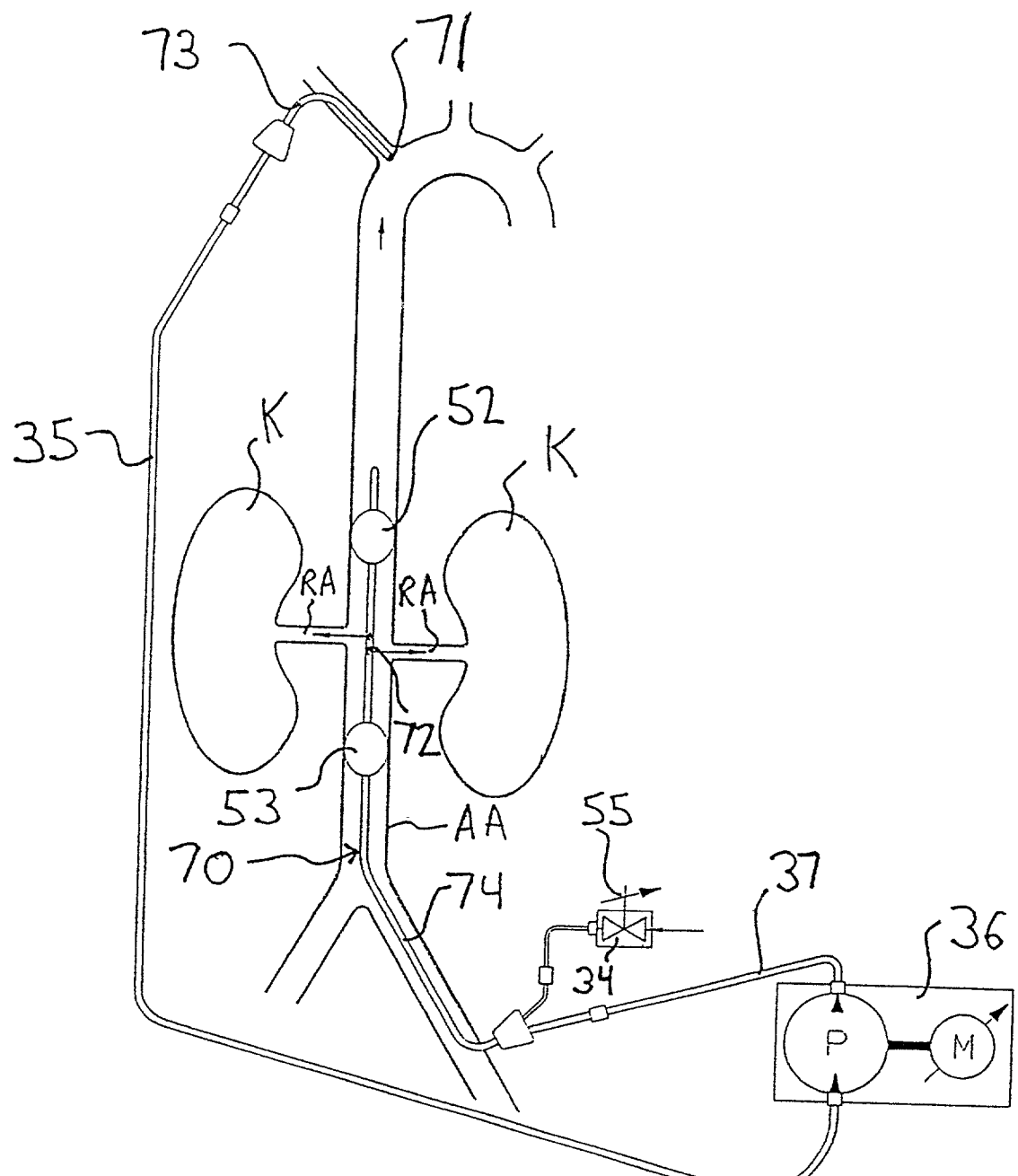
FIG. 5 is a partial sectional view of a human circulatory system having an alternative embodiment of the apparatus of FIG. 3 in which catheter blood flow occurs in one lumen.
Figure 9:
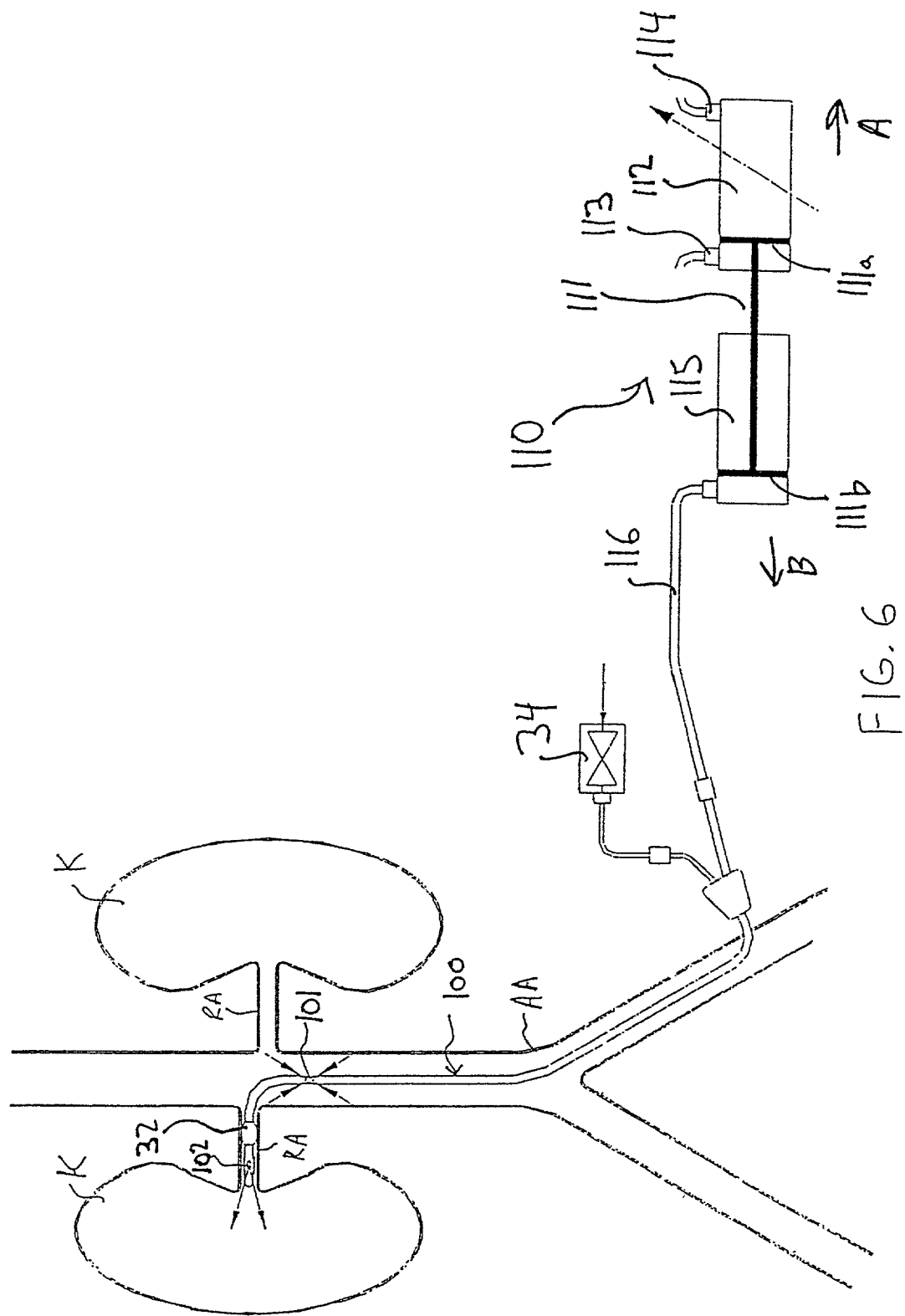
FIGS. 9A and 9B are partial sectional views of the distal end of apparatus labeled with radiopaque markers in, respectively, the inflated and deflated states.

With respect to FIG. 5, a further embodiment of an active perfusion apparatus of the present invention is described. Catheter 70 of FIG. 5 combines elements of catheters 50 and 60. Like catheter 50, catheter 70 employs balloons 52 and 53 controlled by balloon inflation device 34 to periodically isolate a region of the abdominal aorta, including the renal arteries, to permit selective perfusion of the renal arteries. Like catheter 60, catheter 70 includes separate inlet and outlet lines and provides a "once-through" flow path. In particular, blood flows into inlet port 71 of inlet line 73, illustratively placed in the subclavian artery and extending into the aortic arch, through pump inlet tube 35 and to blood pump 36. The blood then is pumped through pump outlet tube 37, outlet line 74 and into renal arteries RA via outlet port 72. As opposed to catheter 60, in which the blood inlet is disposed in the femoral artery, inlet port 71 is instead placed in the aortic arch because the femoral arteries are occluded during inflation of balloons 52 and 53.

As will be obvious to one skilled in the art, catheters 60 & 70 may alternatively withdraw blood from other sources than those illustrated in FIGS. 4 & 5. They may alternatively withdraw blood from a different artery or a different location in the preferred artery. Venous blood perfused in conjunction with saline supersaturated with oxygen or passed through an external oxygenator may also be used.

Figure 7:
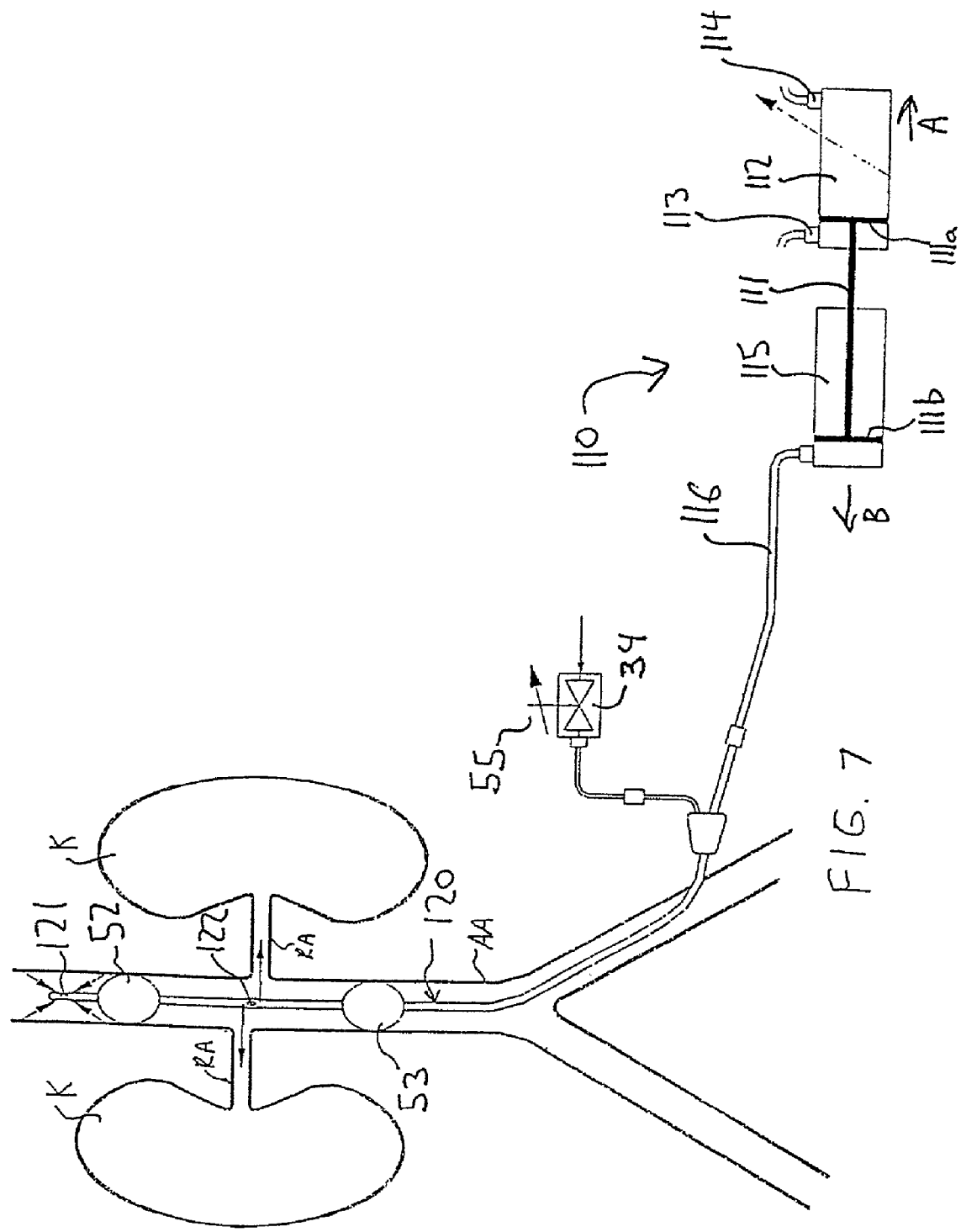
FIG. 7 is a partial sectional view of a human circulatory system having an alternative embodiment of the apparatus of FIG. 3 which perfuses both renal arteries.

Referring to FIGS. 6 and 7, still further embodiments of active perfusion systems of the present invention are described, in which blood is pumped using a periodic displacement method, and no blood is cycled out of the body. Catheter 100 includes balloon 32 coupled to inflation device 34. Catheter 120 includes balloons 52 and 53 coupled to inflation device 34.

Each of catheters 100 and 120 are coupled to extracorporeal pump 110, which causes active perfusion of one or both renal arteries as follows. Pump 110 includes shaft 111 having piston 111a disposed in cylinder 112 and piston 111b disposed in cylinder 115. Piston 111a is displaced by pressurized gas or liquid introduced into cylinder 112 through ports 113 and 114 in an alternating fashion. This, in turn, displaces the shaft 111 and piston 111b in cylinder 115. Cylinder 115 is connected to catheter 100 by connector tube 116.

With piston 111a in its most distal stroke position within cylinder 112 (in direction B), catheter 100 and tube 116 are initially primed with saline solution, so that catheter 100 is initially filled with saline. As pistons 111a and 111b are displaced proximally (in direction A) by the introduction of a pressurized gas or fluid through port 113, movement of piston 111b in direction A causes suction within the saline-filled blood lumen of catheter 100 that draws blood through one-way inlet hole 101 and into the blood lumen. When piston 111b is displaced in direction B by the introduction of a pressurized gas or fluid through port 114, the blood is forced out of one-way outlet hole 102 and into the renal artery. In this manner, renal perfusion is achieved without removing blood from the patient's body.

In FIG. 6, if inlet port 101 and outlet port 102 each include one-way valves, catheter 100 may use s single lumen for blood flow, with operation of pump 110 causing a reversal of flow in the lumen when the direction of piston 111b reverses. As for the previous embodiments, catheter 100 is disposed in circulatory system C so that inlet port 101 is disposed in abdominal aorta AA, while outlet port 102 is disposed in renal artery RA. Balloon 32 is inflated by inflation device 34 to engage the walls of the renal artery and retain port 102 in position.

Likewise, catheter 120 of FIG. 7 also may employ a single blood lumen and one-way valves on the inlet and outlet ports, rather than separate blood inlet and outlet lumens. Operation of catheter 120, including cyclic inflation and deflation of balloons 52 and 53, is otherwise as described hereinabove with respect to catheter 50 of FIG. 3.

Each of catheters 30, 50, 60, 70, 100, and 120 further optionally include a side port (not shown) for coupling the catheter to a drug infusion device, which periodically infuses low doses of therapeutic agents into blood flowing through the catheter. Because the infused drugs are delivered directly into the kidneys, smaller doses may be employed, while achieving enhanced therapeutic action and fewer side-effects.

Figure 8:
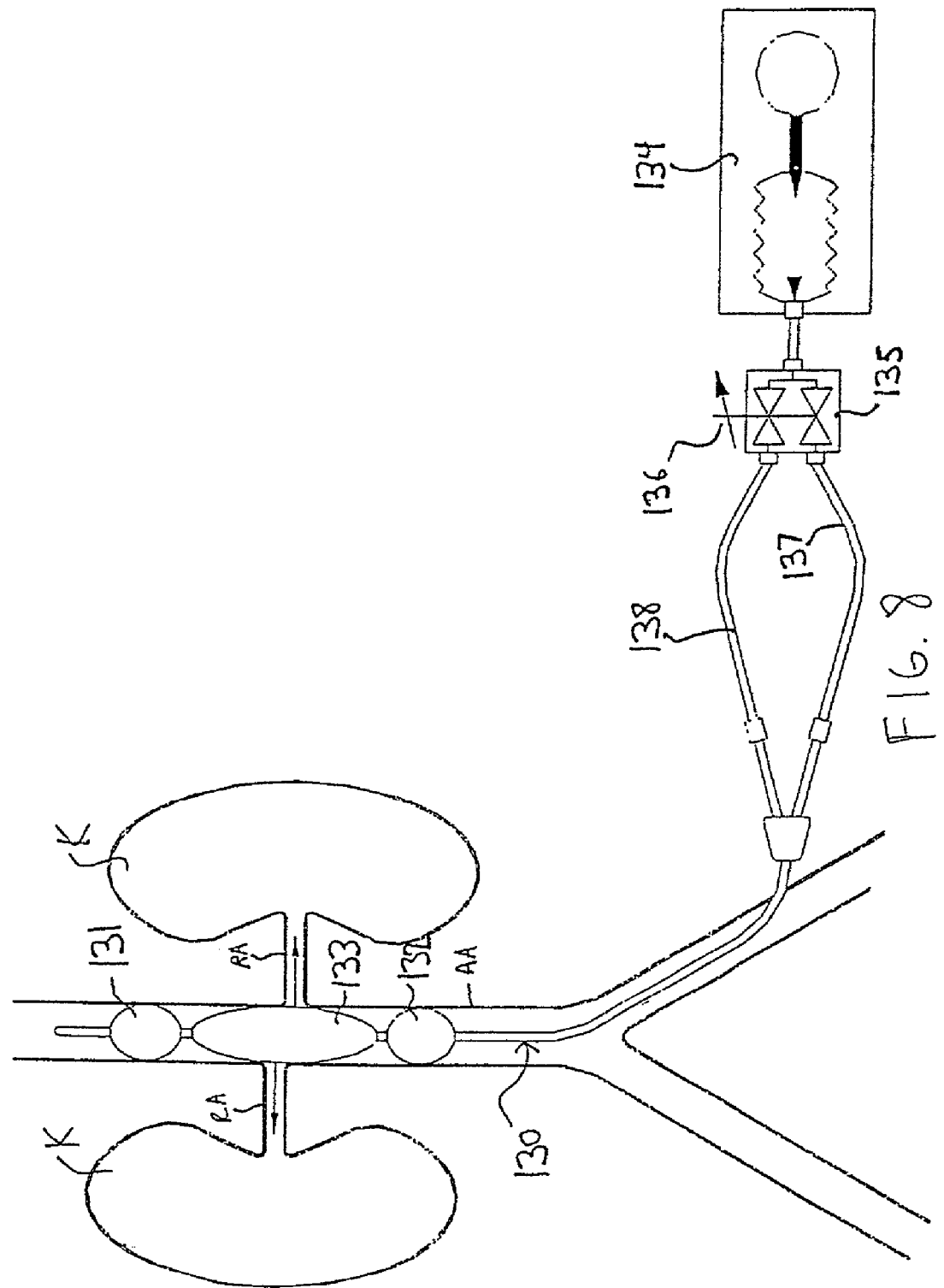
FIG. 8 is a partial sectional view of a human circulatory system having an alternative embodiment of the apparatus of the present invention implanted therein.

In FIG. 8, a further alternative embodiment employing an extracorporeal pump is described. Catheter 130 comprises occlusion balloons 131 and 132 disposed on either side of center balloon 133, pump 134, valve 135, controller 136 and inflation tubes 137 and 138. Valve 135 selectively couples inflation tube 137 and balloons 131 and 132 to pump 134 to inflate and deflate balloons 131 and 132, or couples inflation tube 138 to pump 134 to inflate and deflate center balloon 133.

Each of balloons 131-133 are made of a compliant material, such as polyurethane. Balloons 131 and 132 are spaced apart along catheter 130 so that when the catheter is placed in the abdominal aorta, the balloons straddle the renal arteries, i.e., balloon 131 is disposed above the renal arteries and balloon 132 is disposed below. When fully inflated, balloons 131 and 132 occlude the aorta and isolate the region between the balloons from the proximal and distal portions of the aorta. Balloon 133 is disposed on catheter 130 between balloons 131 and 132 so that it spans the section of AA that branches into the renal arteries.

Catheter 130 includes at least a first inflation lumen that communicates with balloons 131 and 132, and inflation tube 137, and a second inflation lumen that communicates with center balloon 133 and inflation tube 138. Valve 135 is coupled to inflation tubes 137 and 138 to alternately inflate balloons 131 and 132, or center balloon 133, responsive to controller 136. In particular, controller 136 may be configured to inflate and deflate balloons 131 and 132 at a first predetermined time interval, and to inflate and deflate center balloon 133 at a second predetermined time interval. Alternatively, controller may be actuated responsive to the patient's heart rhythm, as determined, for example, by an EKG monitor or blood oximeter.

In operation, catheter 130 is percutaneously and transluminally inserted into a patient's abdominal aorta via a cutdown to the femoral artery. Catheter 130 is disposed, using for example, radiopaque bands near balloons 131-133 visualized under a fluoroscope, so that balloons 131 and 132 are on opposite sides of the junction to the renal arteries. Controller 136 is then actuated to cause valve 135 to couple inflation tube 137 to balloons 131 and 132, thereby inflating those balloons to isolate a region of the abdominal aorta. This in turn traps an amount of blood between balloons 131 and 132 in abdominal aorta AA.

Controller 136 then actuates valve 135 to couple center balloon 133 to pump 134 via inflation tube 138. Inflation of center balloon 133 forces the trapped blood out of abdominal aorta AA into renal arteries RA. All three balloons are then deflated, and the process is repeated. In this manner, renal blood flow and function is enhanced.

Figure 9B:
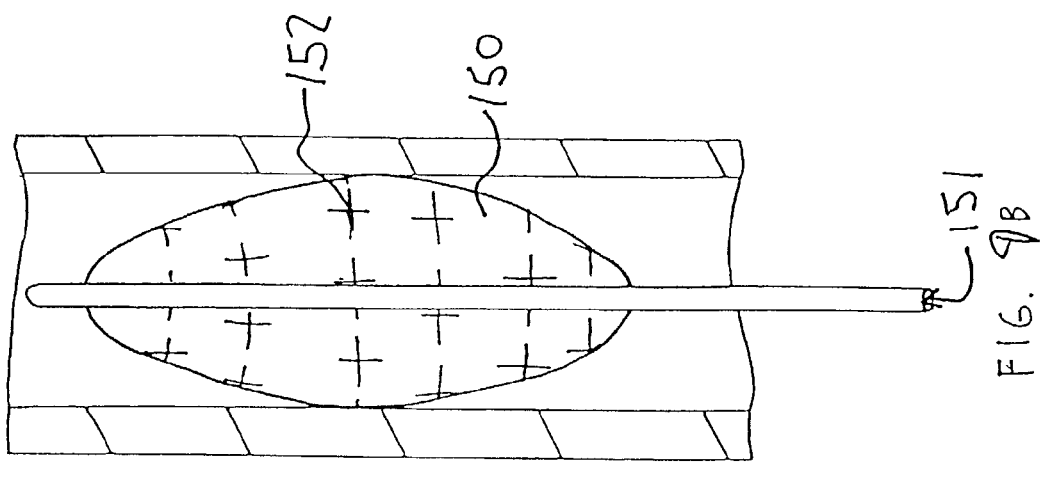
Figure 9A:
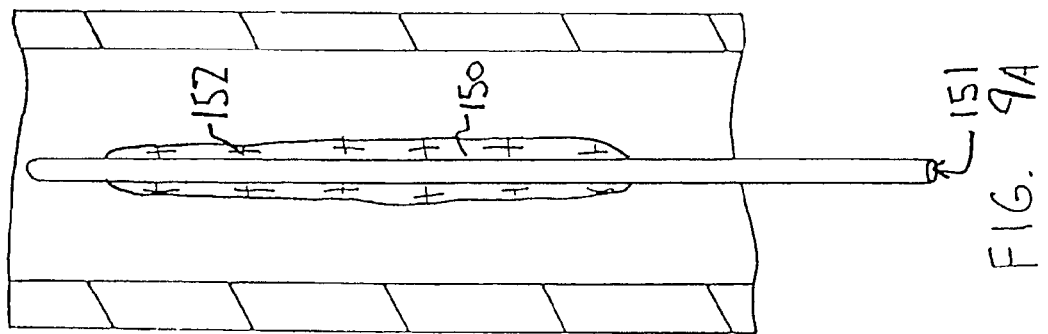

With reference to FIGS. 9A-9B, a further feature of the present invention is described. As will be apparent to those skilled in the art of interventional procedures, precise monitoring and control of the inflation and deflation of the intraaortic balloons is critical to the efficacy of devices that utilize them. FIGS. 9A and 9B depict balloon 150, which may correspond, for example, to balloon 52 of catheter 50, in a deflated state and an inflated state, respectively. Balloon 150 preferably includes radiopaque markers 152. Markers 152 inflate with balloon 150 so as to allow imaging of the balloon during inflation, and a determination of whether or not the balloon is in contact with the blood vessel, illustratively shown as the aortic artery AA. Radiopaque markers 152 advantageously may be used with any of the balloons devices described hereinabove.

Figure 10B:
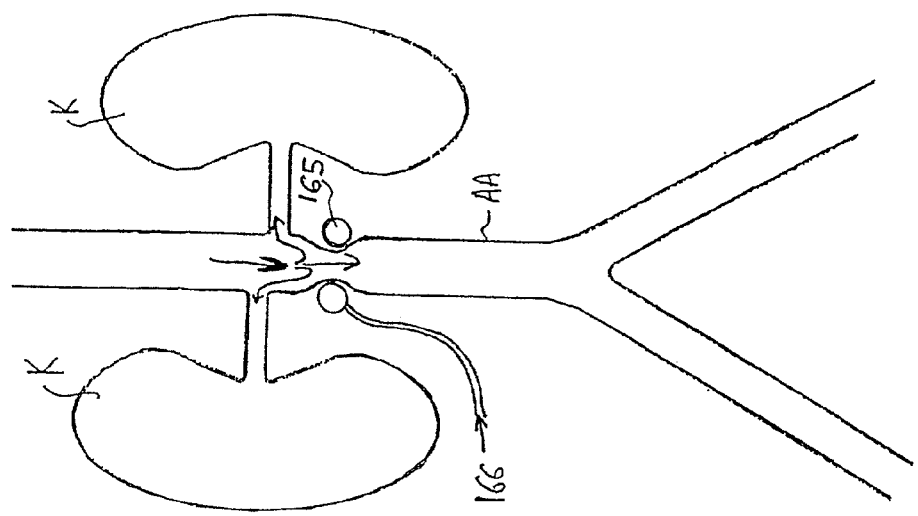
FIGS. 10A and 10B are partial sectional views of a human circulatory system having, respectively, an aortic stent and an inflatable cuff placed proximal of the renal arteries to enhance perfusion.
Figure 10A:
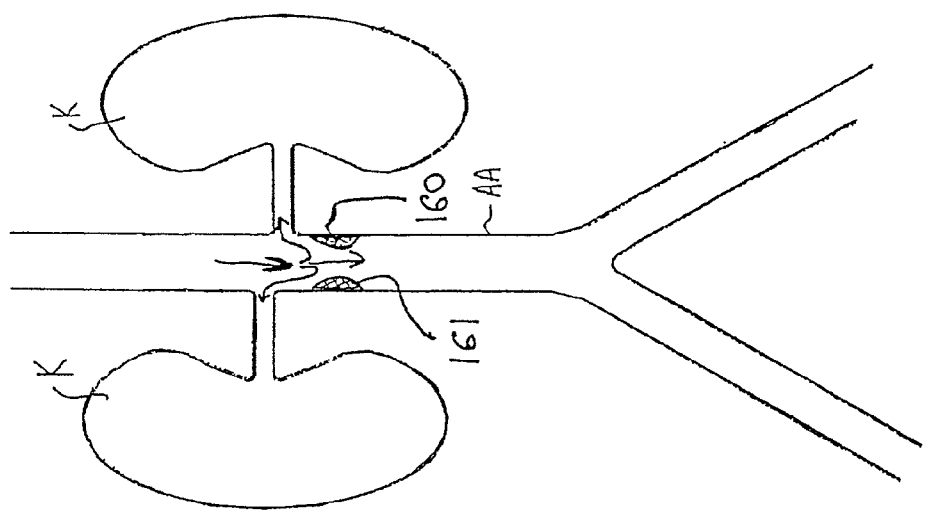

Referring now to FIGS. 10A and 10B, further alternative embodiments of apparatus of the present invention are described that rely upon passive perfusion of the renal arteries. In accordance with this aspect of the present invention, in FIG. 10A stent 160 having constricted region 161 is placed in the aortic artery AA proximal to the renal arteries RA to constrict the aorta below the renal artery junction, and thereby create a pressure differential across the stent. Stent 160 may be constructed for deployment using known techniques, and may be, for example, a self-expanding coiled sheet, tubular member or balloon expandable structure.

Alternatively, for treatment of chronic congestive heart failure, external cuff 165 as shown in FIG. 10B may be placed around the aortic artery AA proximal to the renal arteries RA to constrict the aorta and create the pressure differential across the cuff. Cuff 165 preferably comprises a biocompatible, toroidal balloon. Cuff 165 may be placed using known techniques and may be inflated during or after placement using an inflation medium supplied through lumen 166. Applicants expect that the backpressure created by the constriction imposed by stent 160 or external cuff 165 will improve flow rate to the renal arteries and other proximal organs.

As described hereinabove with respect to the embodiment of FIG. 1, all of the foregoing embodiments, may include sensors at relevant locations to measure pressure or flow related parameters, such as renal and aortic pressure in the system of FIG. 1, or distal and proximal aortic pressures and renal pressure in the system of FIG. 3. Such measurements may then be used to monitor or control perfusion of the kidneys, for example, by adjusting the perfusion pressure or blood flow rate.

Figure 11:
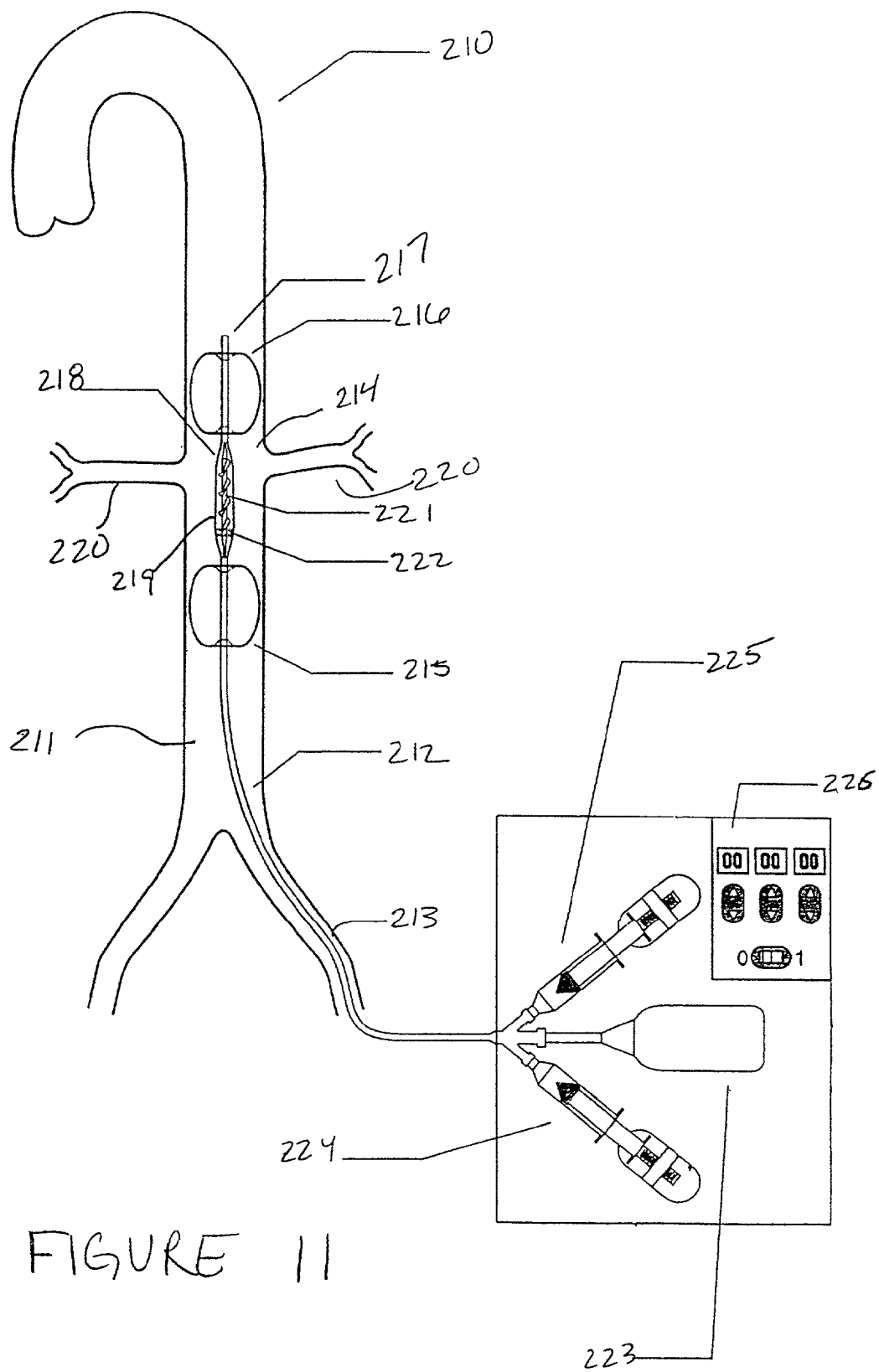
FIG. 11 is an elevational view of a catheter partially in section of a catheter embodying features of the invention including an archimedean screw pump disposed with a patient's abdominal aorta.

One preferred embodiment is shown at FIGS. 11-15. FIG. 11 shows a catheter 211 embodying features of the invention disposed within a patient's aorta 210. The catheter 211 has an elongated shaft 212 having a proximal end 213 and a distal end 214. The balloon distal end 214 has two occlusion balloon, proximal balloon 215 and distal balloon 216, disposed about a portion. Proximal balloon 215 is positioned below the patient's renal arteries 220, while distal balloon 216 is positioned above the renal arteries 220. Proximal balloon 215 distal end is about 5 cm to about 15 cm from distal balloon 216 proximal end, preferably about 5 to about 10 cm. Both proximal balloon 215 and distal balloon 216 are capable of inflation to about 20 to about 30 millimeters outside diameter. The catheter distal end 214 also includes a blood inlet 217. Between balloon 215 and 216 is located an archimedean screw pump 218. Screw pump 218 includes a housing 219, a rotor 221 and a seal 222. The seal 222 may or may not let blood pass. The catheter proximal end 213 includes a drive mechanism 223. The drive mechanism may be a DC, AC or pneumatic motor capable of maintaining high speed, about 5000 to about 30,000 rpm, and moderate torques for periods lasting at least 20 minutes. Also connected to the catheter proximal end 213 are inflation sources 224 and 225 for proximal balloon 215 and distal balloon 216 respectively. The screw pump 218 may be controlled automatically by an autocontroller 226, which may also be automated to control the inflation of the proximal balloon 215 and the distal balloon 216.

Figure 12:
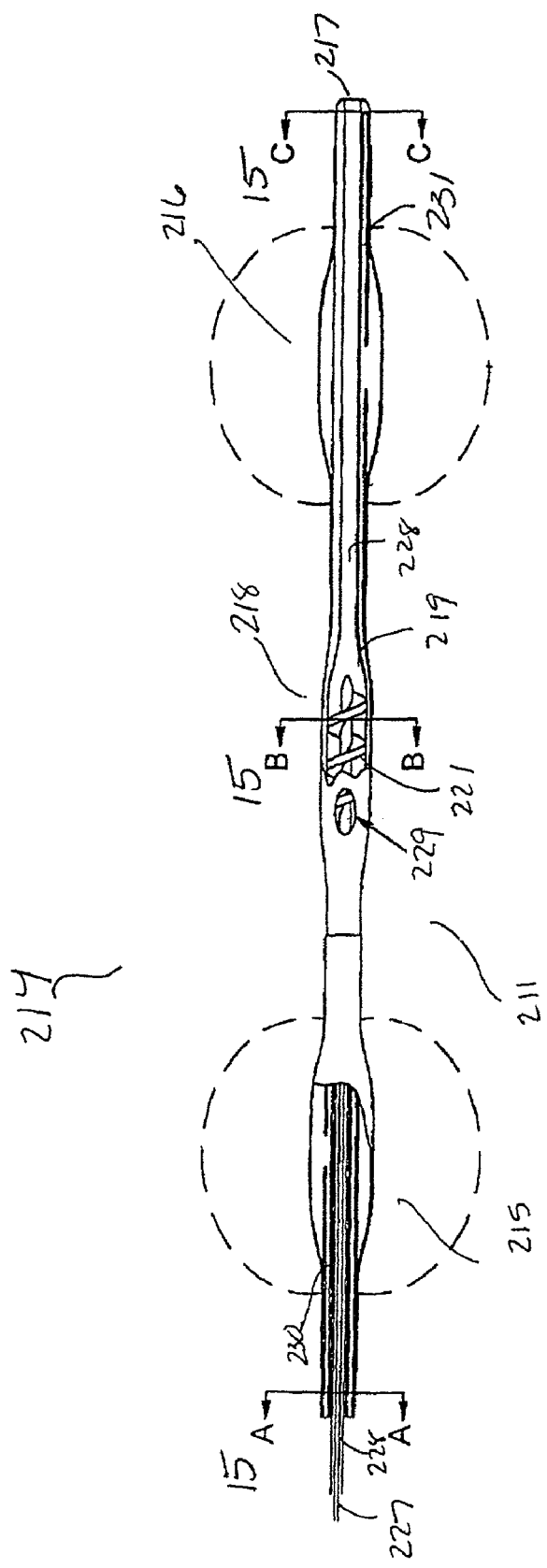
FIG. 12 is an elevational view partially in section of a catheter embodying features of the invention including an archimedean screw pump.

FIG. 12 better illustrates the inner workings of catheter 211 at the catheter distal end 214. A drive shaft 227 is located within main lumen 228. The drive shaft 227 is connected to the drive mechanism 223 on its proximal and, and the screw pump 218 in its distal end. The drive mechanism 223 turns the drive shaft 227, which then turns the rotor 221. Blood enters the catheter 211 through the inlet 217 and travels to the screw pump housing 219. The rotor 221 turns, causing a pressure increase within the housing 219. Blood then exits out the blood outlet 229 at a higher pressure. As was shown in FIG. 11, the housing is located near the renal arteries 220. Therefore, blood exits from the housing 219 through blood outlet 229 into the renal arteries 220. More than one blood outlet may be disposed about the radial face of the catheter shaft 212. Blood flows in total at a rate of about 600 ml/min to about 1200 ml/min, preferably about 800 to about 1200 ml/min out the blood outlet 229 into the abdominal aorta 210. This higher pressure blood then moves through the renal arteries 220, which are constricted causing ARF. In an alternative embodiment, the seal 222 may allow some blood to pass into the main lumen 228. An additional blood outlet then may be provided proximal to proximal balloon 215, thereby providing blood to the lower extremities. This may also be accomplished by providing a blood pass through lumen in addition to the lumen shown in this embodiment (not shown). As screw pump 218 is causing high pressure blood to exit the blood outlet 229, the proximal balloon 215 and distal balloon 216 may be inflated. The balloons 215 and 216 may also be inflated prior to the screw pump 218 activation. The inflation source 224 is activated, and an inflation fluid enters inflation lumen 230, which is in fluid communication with proximal balloon 215. Either simultaneously or at a desired time, inflation source 225 is activated, sending an inflation fluid into inflation lumen 231, which is in fluid communication with distal balloon 216. The balloons 215 and 216 inflate against the aorta 210 to a final outer diameter indicated in phantom, thereby isolating the area surrounding the renal arteries 220. This allows the increased pressure caused by the pump to be most effective. Higher pressure blood will be more likely to enter the renal arteries 220, thereby effectively perfusing the constricted renal arteries 220. In embodiments which do not include a blood pass through lumen (not shown) or all blood to flow past the seal 222, the balloons 215 and 216 may be deflated periodically to allow blood flow to the lower extremities, or occlusion may be controlled such that some blood leaks by the balloons 215 and 216 without compromising pressure in the renal arteries 220.

The drive shaft 227 may be a flexible component to accomplish torque transmission from the motor to the rotor and overcome any curvature of the catheter shaft imparted by the vasculature. The drive shaft 227 may be made of a coiled wire or a flexible mandrel or a combination of these, possibly of stainless steel or superelastic nitinol. The drive shaft 227 may be coated with a low friction and high temperature resistant material such as Teflon. The engagement between the drive mechanism 223 and the drive shaft 227 may be accomplished by means of a threaded connection, set screw and collar connection, or a snap fit engagement. The drive shaft 227 may be press fit, welded, threaded, or adhesive bonded to the rotor 221.

Figure 13:
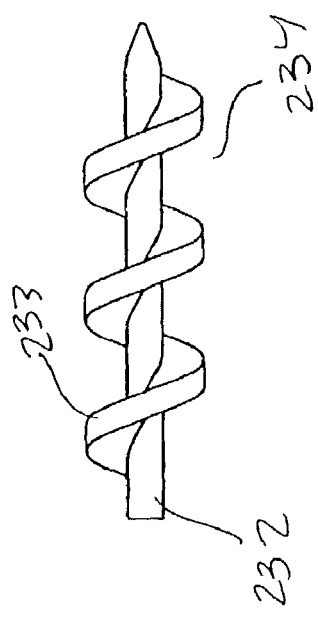
FIG. 13 is an elevational view of an archimedean screw.
Figure 14:
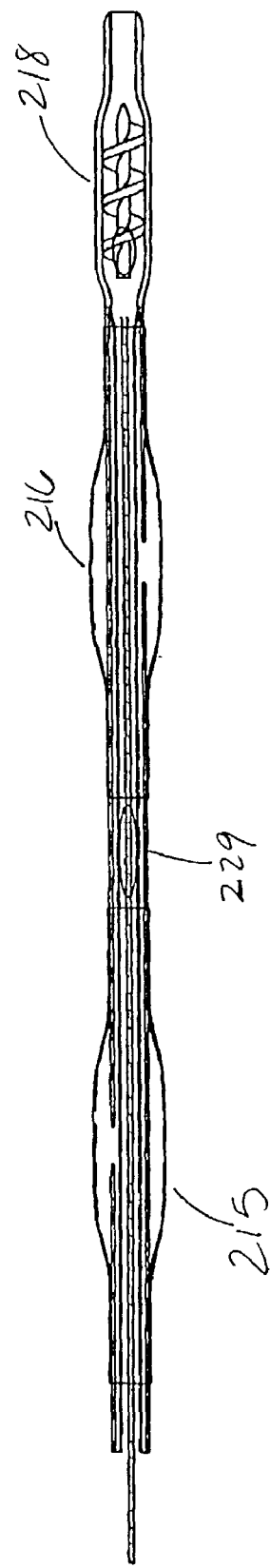
FIG. 14 is an elevational view, partially in section, of an alternative embodiment of the catheter of the invention including the archimedean screw pump.
Figure 15C:
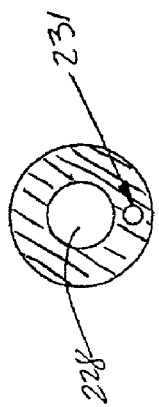
FIGS. 15A, 15B and 15C are transverse cross sectional views of the catheter of FIG. 12 along lines 15A-A, 15B-B and 15C-C respectively.
Figure 15B:
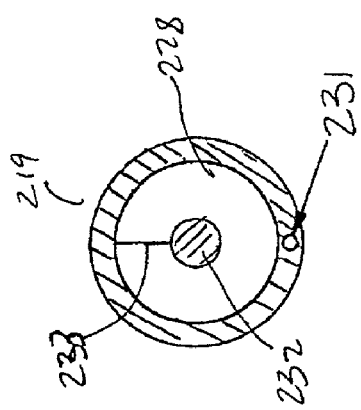
Figure 15A:
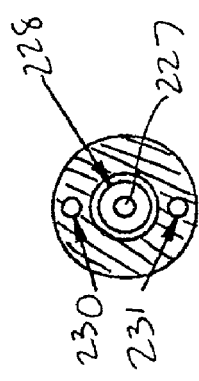
Figure 17:
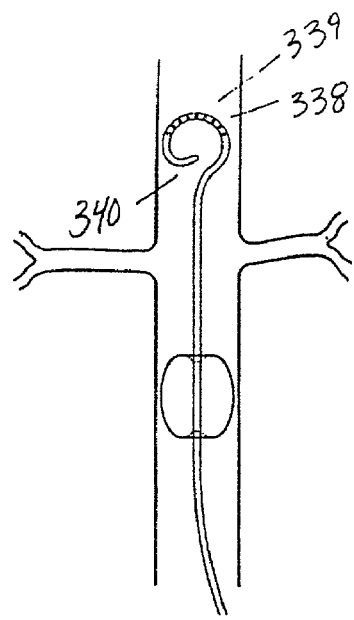
FIG. 17 is an elevational view of an alternative embodiment of a catheter embodying features of the invention including a drug delivery system.
Figure 18:
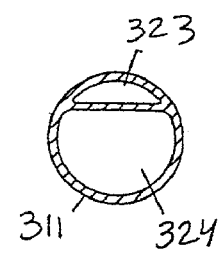
FIG. 18 is a transverse cross sectional view of the catheter of FIG. 16 along line 18-18.
Figure 19:
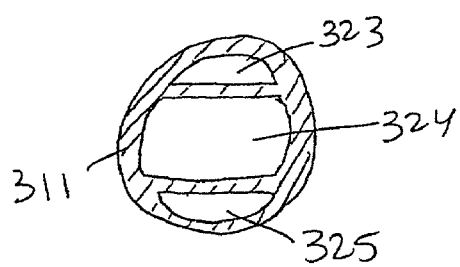
FIG. 19 is an alternative transverse cross sectional view of the catheter of FIG. 16 along line 18-18.

FIG. 13 is a detailed view of the screw pump rotor 221. The rotor is a single helix rotor having a hub 232 and a blade 233. The rotor generally is about 1 cm to about 5 cm, preferably about 2 cm to about 4 cm long. The diameter of the rotor is about 0.1 inch to about 0.25 inch, preferably about 0.15 inch to about 0.2 inch. The distance on the hub 232 between blade 233 turns may be uniform. In some embodiments, the distance between blade 233 turns is not uniform. In certain embodiments, the rotor is a single helix progressive pitch rotor, and the kick area 234 has a greater distance on the hub 232 between blade 233 turns. FIG. 14 illustrates an alternative embodiment of the catheter of the invention, wherein the screw pump 218 is located distal to the distal balloon 216. Blood outlet 229 is still located between proximal balloon 215 and distal balloon 216.

The rotor 221 may be an overall cylindrical component consisting of a helical blade 233 around a hub 232 designed to transfer rotational motion of the rotor to translational motion of the blood. 1-5 helical blade components, preferably 1-3 helical blade components may wrap the hub 232 of the rotor. The hub 232, will be minimized to increase the blood volume capacity between the blades 233. A progressive pitch, or variable, pitch blade may be used to gradually accelerate the blood along the length of the rotor 221. The helix may progress from a high pitch to low pitch configuration the last of which is known as the kick of the blade 234. Maximizing acceleration of the blood while minimizing possible cavitation or hemolysis within the system is preferred. The rotor 221 may be machined, injection molded, or cast as one component or assembled from multiple parts, such as separate blade and core components. The rotor 221 may be made of metal or plastic. The rotor 221 will be encased within a housing designed to confine the travel of the blood to a translational volume exchange. The housing 219 may be cylindrical and fit closely with the diameter of the rotor 221. The housing 219 and rotor 221 will work together to maximize the translational motion of the blood and control the centrifugal forces imparted on the fluid. The housing 219 may be constructed of a metal or plastic. The housing 219 will be a bearing surface for the rotor blades 233 and will be required to withstand the forces and temperatures generated by the rotor 221. It may be a portion of the catheter shaft 212 in which the rotor 221 is housed but not a separate component requiring connection to the catheter shaft 212. If the housing 219 is a separate component it may be secured to the catheter shaft 212 by heat fusing, adhesive bonding, chemically welding, or barb fitted. The housing 219 of the screw pump 218 will be at least as long as the rotor 221 and may taper at either end of the rotor 221 to optimize the intake and outlet volume of the pumping area.

The centrifugal force imparted on the blood by the rotor will help the blood progress toward the outlet do to its placement along the outer diameter of the catheter shaft. A backpressure will be created within the central lumen of the catheter to prevent the flow of blood beyond the outlet. This backpressure will be created either by a o-ring tip seal between the central lumen ID and drive shaft or by a pressurized fluid flow within the annular space between the drive shaft and catheter ID. This fluid will also serve to reduce temperatures created by the spinning components. The fluid may be saline or dextrose and may be heparinized.

Another preferred embodiment is disclosed in FIGS. 16-19. FIG. 16 shows a catheter 311 embodying features of the invention placed within a patient's aorta 310. The catheter has a shaft 312, a proximal end 313 and a distal end 314. Shaft 312 may include markers along the length to assist a user in proper placement. (not shown). Such markers are especially helpful along the proximal end 313, to aid in placement without the use of X-ray fluoroscopy guidance. The distal end 314 includes a distal tip portion 315. Distal tip portion 315 is placed above the patient's renal arteries 320. The distal end 314 additionally includes an inflatable balloon 316. Inflatable balloon 316 is placed below the patient's renal arteries 320. Inflatable balloon 316 is about 5 cm to about 20 cm from the distal tip portion 315, preferably about 10 cm to about 15 cm. The distal tip portion 315 includes discharge ports 317. Discharge ports may be formed of slits. In an alternative embodiment illustrated in FIG. 17, the discharge ports 317 are sideholes 338, placed along a pigtail shaped distal tip portion 339 with a tapered closed tip 340. If the distal tip portion 315 of the catheter 311 is closed, it may be sealed or include a sealing surface which mated with an obturator or a stiffening mandrel. In such an even, it may become necessary to use a duck-billed valve to provide for guidewire passage without losing the fluid seal.

The proximal end 313 is connected to a system console 318. The system console 318 includes an inflation source 321 and a drug delivery source 322. Inflation source 321 is in fluid communication with inflation lumen 323. An inflation fluid travels through inflation lumen 323, which is in fluid communication with the inflatable balloon 316, and inflates inflatable balloon 316. Drug delivery source 322 is in fluid communication with drug delivery lumen 324. A drug may be introduced into the drug delivery lumen 324 and travels to the distal tip portion 315. At the distal tip portion 315, the drug delivery lumen 324 is in fluid communication with the discharge ports 317, thereby discharging the drug into the patient's aorta 310. In alternative embodiments, the catheter 311 additionally includes a blood pass through lumen 325. The blood pass through lumen 325 will have an inlet port on the distal tip portion 315 (not shown) and an outlet situated on the catheter proximal to the balloon (not shown) to supply blood to the lower extremities during balloon inflation.

Figure 20:
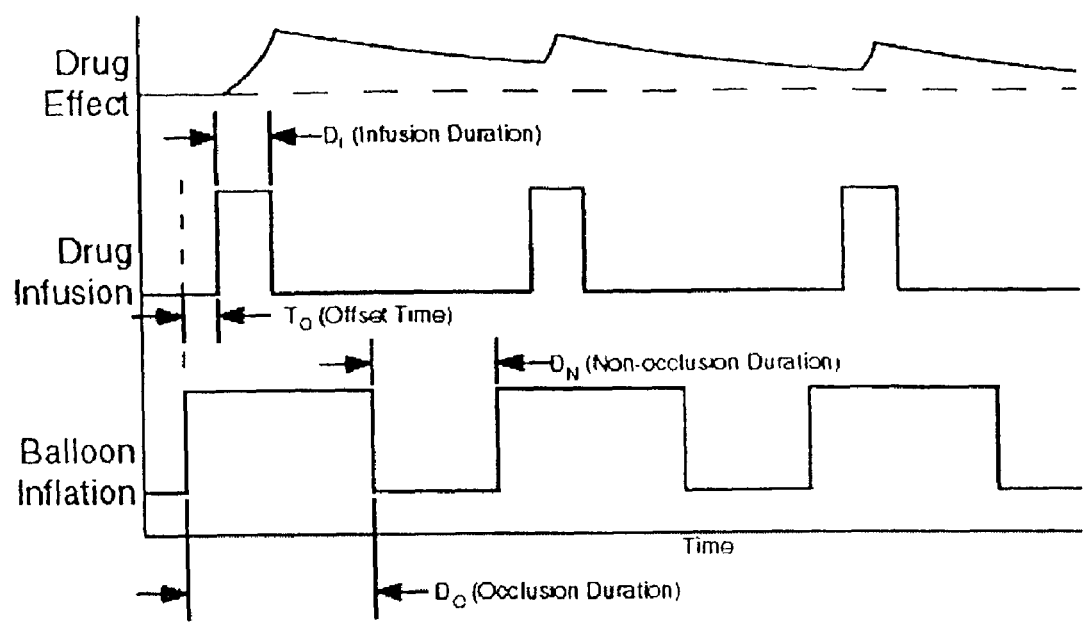
FIG. 20 is a graphical representation of the balloon inflation and deflation during drug infusion and the drug's affect on the renal arteries.

The systems console 318 additionally includes an autocontrol device 319. An example of such an autocontrol device would be a microprocessor-control module with a user interface. FIG. 20 illustrates the benefit of including an autocontrol device 319 in the system console 318. The balloon 316 may be inflated periodically to correspond to drug delivery. Therefore, the drug will be directed into the patient's renal arteries 320 because the balloon 316 has isolated the renal arteries 320. This allows for a localized delivery of a drug to the renal arteries 320 without having a system-wide effect on the patient's body. A preferred drug for this apparatus would include a drug which is a short-acting vasodilator.

As illustrated in FIG. 20, the delivery of the drug will by synchronized with the aortic occlusion to divert the blood flow and infused drug to the renal arteries. The time lag between the beginning of balloon inflation and the beginning of drug infusion in a cycle is called T1. The lag time between the end of drug infusion and balloon deflation is called T2. The balloon will occlude the aorta in order to deliver a high amount of drug to the renal arteries, and only a minor amount to the lower extremities. The therapy will be automated to keep the drug level in the renal arteries at a set minimum to ensure increased renal perfusion is sustained. The drug may be delivered in increasingly small amounts, as well, as therapy progresses and the reduce the patient's risk of systemic effects of too much drug.

While preferred illustrative embodiments of the invention are described-above, it will be apparent to one skilled in the art that various changes and modifications may be made therein without departing from the invention, and the appended claims are intended to cover all such changes and modifications that fall within the true spirit and scope of the invention. Additionally, although various features of the invention are disclosed in specific embodiments, one or more of the features may be used and exchangeable in other embodiments disclosed herein.

What is claimed is:

1. A method of enhancing perfusion to a patient's kidneys in vivo, the method comprising: providing a catheter having first, second and third balloons, the third balloon disposed between the first and second balloons; placing the-catheter in the patient's aorta so that the first and second balloons straddle a region of the aorta including the patient's junction to the renal arteries; inflating the first and second balloons to trap an amount of blood within the region and isolate the region; inflating the third balloon to direct the trapped blood into the renal arteries.

2. The method of claim 1 further comprising deflating the first, second and third balloons to re-establish blood flow through the aorta.

* * * * *